United States Patent

Baumann et al.

[11] 4,029,677
[45] June 14, 1977

[54] SPIRODIPYRANS USEFUL AS DYE PRECURSORS FOR COPYING PROCESSES

[75] Inventors: Hans Baumann; Andreas Oberlinner, both of Ludwigshafen, Germany

[73] Assignee: BASF Aktiengesellschaft, Ludwigshafen, Germany

[22] Filed: June 5, 1975

[21] Appl. No.: 584,066

[30] Foreign Application Priority Data

June 26, 1974 Germany .................. 2430568

[52] U.S. Cl. .................. 260/345.2; 260/345.5; 96/48 R; 96/90 PC; 96/48 QP; 96/90 R; 96/88; 96/1.5; 8/7

[51] Int. Cl.² ............. C07D 311/02; C07D 311/72

[58] Field of Search .................. 260/345.2, 345.5

[56] References Cited

UNITED STATES PATENTS

| | | | |
|---|---|---|---|
| 2,978,462 | 4/1961 | Berman et al. | 260/345.2 |
| 3,022,318 | 2/1962 | Berman et al. | 260/345.2 |
| 3,666,525 | 5/1972 | Kimura et al. | 260/345.2 |
| 3,810,762 | 5/1974 | Laridon et al. | 260/345.2 |
| 3,810,763 | 5/1974 | Laridon et al. | 260/345.2 |
| 3,896,126 | 7/1975 | Oberlinner et al. | 260/345.2 |
| 3,899,514 | 8/1975 | Baumann et al. | 260/345.2 |

FOREIGN PATENTS OR APPLICATIONS 2,232,364  3/1974  Germany ............... 260/345.2

*Primary Examiner*—James O. Thomas, Jr.
*Assistant Examiner*—Nicky Chan
*Attorney, Agent, or Firm*—Keil, Thompson & Shurtleff

[57] ABSTRACT

New spirodipyrans of the formula

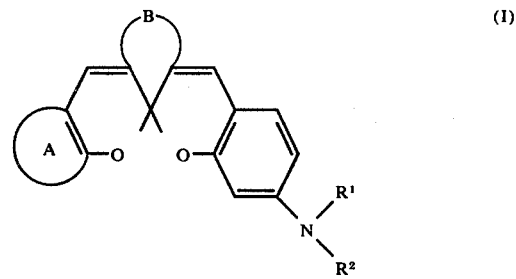

in which A is an optionally substituted benzene or naphthalene nucleus, B is dimethylene, trimethylene or tetramethylene substituted by from 1 to 3 alkyl groups and $R^1$ and $R^2$ are each alkyl of 1 to 6 carbon atoms, which may be substituted by cyano. The compounds (I) give deep blue to violet colorations with acid materials. They may be used for the manufacture of pressure-sensitive recording materials. The compounds (I) exhibit improved solubility in the solvents used for the manufacture of microcapsules.

10 Claims, No Drawings

SPIRODIPYRANS USEFUL AS DYE PRECURSORS FOR COPYING PROCESSES

The present invention relates to new spirodipyrans and their use as dye precursors for copying processes.

The new spirodipyrans have the formula

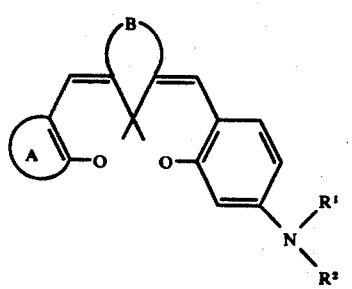 (I)

in which A is an unsubstituted benzene or naphthalene nucleus or a benzene or naphthalene nucleus substituted by 1 or 2 alkyl of 1 to 4 carbon atoms, chlorine, bromine, alkoxy of 1 to 4 carbon atoms or carbalkoxy of a total of 2 to 5 carbon atoms, B is dimethylene, trimethylene or tetramethylene substituted by from 1 to 3 alkyl of a total of 1 to 12 carbon atoms and $R^1$ and $R^2$ are identical or different alkyl each of 1 to 6 carbon atoms, which may be substituted by cyano.

The spirodipyrans of the formula I are colorless or pale compounds. Their solution in non-polar or slightly polar solvents, such as hydrocarbons, chlorohydrocarbons or esters, give deep blue or violet coloration on addition of acid materials. Since this reaction is also brought about by kaolin, zeolites, bentonite, silica, aluminum oxide and phenolic condensation products, the new compounds (I) may be used as dye precursors for pressure-sensitive recording materials, particularly for the manufacture of copying papers.

The group

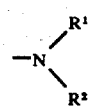

is preferably dimethylamino or diethylamino, but may also be dipropylamino, N-methyl-N-β-cyanoethylamino or N-ethyl-n-β-cyanoethylamino.

Specific examples of B are methyldimethylene —CH$_2$—CH(CH$_3$)—, trimethylene of the formula

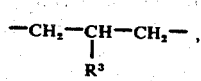

in which $R^3$ is tert.-butyl, methyl, butyl, hexyl, octyl, nonyl, decyl or dodecyl, trimethyltrimethylene —C(CH$_3$)$_2$—CH$_2$—CH(CH$_3$)— and trimethyltetramethylene —C(CH$_3$)$_2$—CH$_2$—CH(CH$_3$)—CH$_2$—.

Spirodipyrans in which B is trimethylene substituted by from 1 to 3 alkyl are preferred. Particularly preferred substitutents of B are three methyl, or tert.-butyl, octyl, nonyl and dodecyl.

In the formula I, A may be an unsubstituted benzene or naphthalene nucleus but also a benzene nucleus substituted by one chlorine, bromine, methyl, methoxy or two methyl or a naphthalene nucleus substituted by one bromine or chlorine, or by one carboalkoxy, such as carbomethoxy, carboethoxy, carbopropoxy or carbobutoxy.

If A is a benzene nucleus, the substituents are preferably in the 8-, 6-and/or 5-position, whilst in the case of the naphthalene nucleus they are preferably in the 5-, 7-, 8- or 10-position.

From the technical, tinctorial and applications points of view, the compounds of the formulae

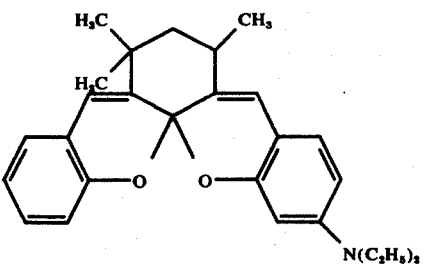

and

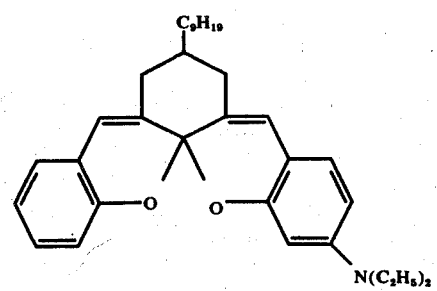

are very particularly preferred.

The spiropyrans of the formula I may be manufactured by a conventional method, by condensation of benzopyrylium salts or naphthopyrylium salts of the formula II or the corresponding o-hydroxyarylmethinecylcoalkyliden-2-ones of the formula III with N-substituted p-aminosalicylaldehydes of the formula IV, or from the compounds of the formula VI and o-hydroxyaldehydes of the formula V, in accordance with the following equations:

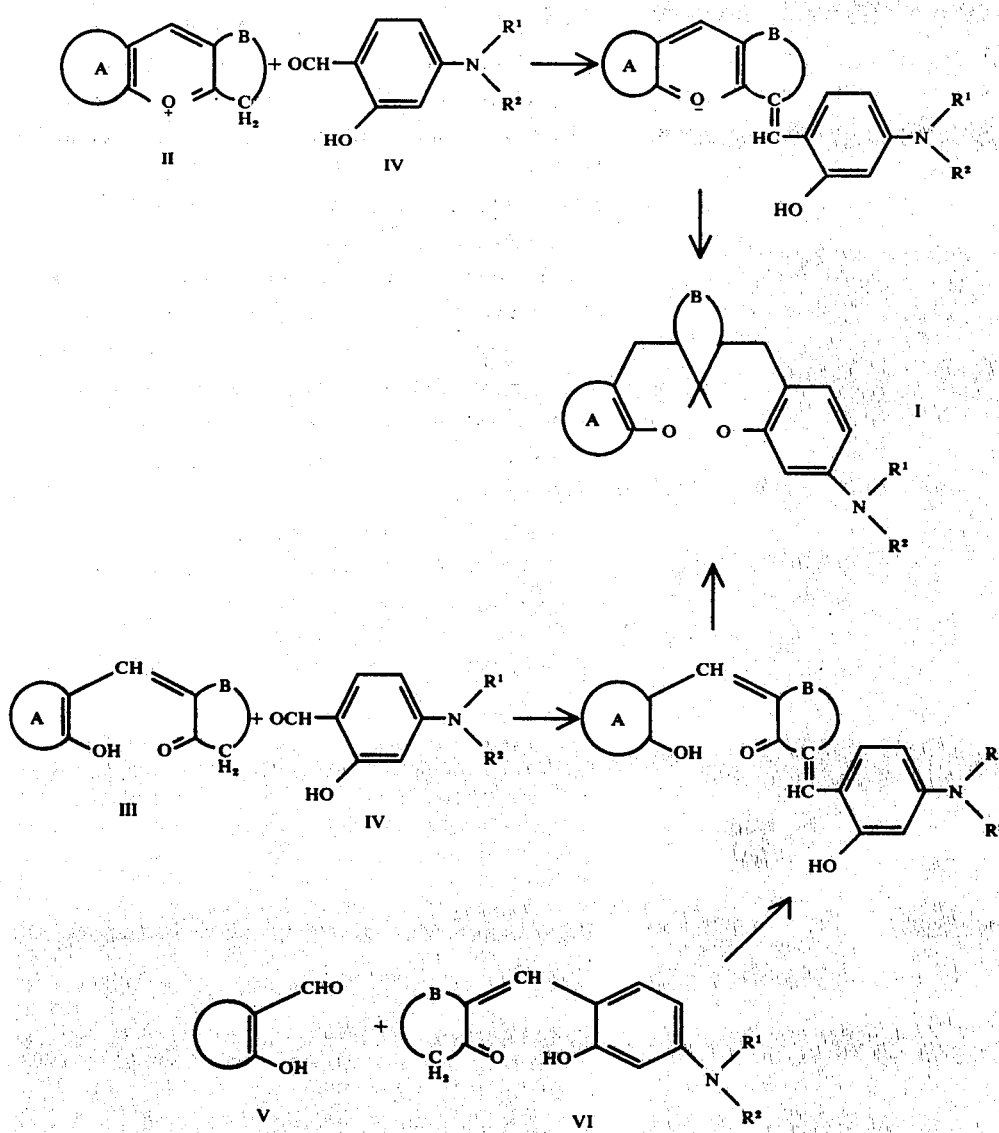

Specific examples of starting materials which may be used are:

Amongst pyrylium salts of the formula II, in the form of their chlorides, perchlorates, tetrafluoborates, tetrachloroferrates or trichlorozincates: 2,3-(γ-tert.-butyltetramethylene)-benzopyrylium salts, 2,3-(γ-dodecyltetramethylene)-benzopyrylium salts, 2,3-(γ-tert.-butyl-tetramethylene)-6-chlorobenzopyrylium salts, 2,3-(γ-tert.-butyl-tetramethylene)-6-bromobenzopyrylium salts, 2,3-(β,δ,δ-trimethyl-tetramethylene)-benzopyrylium salts, 2,3-(γ-octyl-tetramethylene)-benzopyrylium salts, 2,3-(γ-nonyltetramethylene)-benzopyrylium salts, 2,3-(γ-tert.-butyl-tetramethylene)-8-methoxy-benzopyrylium salts, 2,3-(γ-tert.-butyl-tetramethylene)-8-methoxy-benzopyrylium salts, 2,3-(γ-tert.-butyltetramethylene)-5,6-dimethylbenzopyrylium salts, 2,3-(γ-tert.-butyl-tetramethylene-6,7-dimethyl-benzopyrylium salts, 2,3-(γ-tert.-butyl-tetramethylene)-naphtho-[2,1-b]-pyrylium salts, 2,3-(γ-tert.-butyl-tetramethylene-7-bromonaphtho-[2,1-b]-pyrylium salts, 2,3-(γ-tert.-butyl-tetramethylene)-8-bromonaphtho-[2,1-b]-pyrylium salts, 2,3-(γ-tert.-butyl-tetramethylene)-10-carbomethoxy-naphtho-[2,1-b]-pyrylium salts, 2,3-(γ-tert.-butyl-tetramethylene)-5-carbomethoxy-naphtho-[2,1-b]-pyrylium salts, 2,3-(γ-octyl-tetramethylene)-naphtho-[2,1b]-pyrylium salts, 2,3-(β-methyl-trimethylene)-benzopyrylium salts, 2,3-(β-methyltrimethylene)-naphtho-[2,1-b]-pyrylium salts and 2,3-(γ, ε,ε-trimethyl-pentamethylene)-benzopyrylium salts.

Amongst aldehydes of the formula IV: 2-hydroxy-4-dimethylaminobenzaldehyde, 2-hydroxy-4-dimethylaminobenzaldehyde, 2-hydroxy-4-dipropylaminobenzaldehyde, 2-hydroxy-4-(N-methyl-β-cyanoethylamino)-benzaldehyde and 2-hydroxy-4-(N-ethyl-β-cyanoethylamino)-benzaldehyde.

Amongst o-hydroxyarylmethine-cycloalkyliden-2-ones of the formula III: o-hydroxyphenyl-5-tert.-butylmethine-cyclohexyliden-2-one, o-hydroxy-m-chlorophenyl-5-tert.-butylmethine-cyclohexyliden-2-one, o-hydroxy-m-bromophenyl-5-dodecylmethine-cyclohexyliden-2-one, o-hydroxynaphtyl-(1)-5-tert.-butylmethine-cyclohexyliden-2-one, o-hydroxyphenyl-4-methylcyclopentyliden-2-one and o-hydroxyphenyl-5,7,7-trimethylcycloheptyliden-2-one.

Amongst compounds of the formula V: salicylaldehyde, 2-hydroxy-5-chlorobenzaldehyde, 2-hydroxy-5- bromobenzaldehyde, 2-hydroxy-3-methoxybenzaldehyde, 2-hydroxy-4,5-dimethylbenzaldehyde, β-hydroxynaphthaldehyde, 2-hydroxy-3-carbomethoxy-1-naphthaldehyde, 2hydroxy-3-carboethoxy-1naphthaldehyde and 2-hydroxy-6-bromo-1-naphthaldehyde.

Amongst compounds of the formula VI: o-hydroxy-β-dimethylaminophenyl-5-tert.-butylmethine-cyclohexyliden-2-one, o-hydroxy-p-diethylaminophenyl-5-octylmethine-cyclohexyliden-2-one, o-hydroxy-p-dimethylaminophenyl-5-octylmethine-cyclohexyliden-2-one, o-hydroxy-p-diethylaminophenyl-5-dodecylmethine-cyclohexyliden-2-one, o-hydroxy-p-dimethylaminophenyl-5-dodecylmethine-cyclohexyliden-2-one, o-hydroxy-p-dimethylaminophenyl-5-nonylmethine-cyclohexyliden-2-one, o-hydroxy-p-diethylaminophenyl-5-nonylmethine-cyclohexyliden-2-one, o-hydroxy-p-diethylaminophenyl-5-tert.-butylmethine-cyclohexyliden-2-one, o-hydroxy-p-diethylaminophenyl- b 4-methylmethine-cyclopentyliden-2-one and o-hydroxy-p-diethylaminophenyl-5,7,7-trimethyl-cycloheptyliden-2-one.

The condensation is conveniently carried out in organic solvents which are liquid at the reaction temperature, e.g. alcohols, carboxylic acids, carboxylic acid anhydrides, carboxylic acid amides, hydrocarbons or acetonitrile, if appropriate in the presence of acid or basic condensing agents, such as zinc chloride, phosphoric acid, toluenesulfonic, acid, boric acid, pyridine, piperidine, triethylamine and ammonium acetate. The amount of condensing agent is usually from 0.1 to 10 percent by weight, based on (II), and is accordingly within the conventional range for condensations of the type in question. The condensation is carried out by conventional methods, advantageously at from 20° to 120° C.

The cyclization to the pyran may be carried out by conventional methods, simultaneously with the condensation or subsequently thereto, in the same process step or a separate step, if appropriate in the presence of bases, such as sodium hydroxide or potassium hydroxide, sodium carbonate or potassium carbonate, sodium acetate or potassium acetate, ammonia, aliphatic amines or pyridine. The crystalline spirodipyran compounds which separate out from this solution may be used as dye precursors for copying processes.

By way of example, the spirodipyrans may be converted to a paste which is spread on paper, after which the surface is provided with a protective coating. A particularly advantageous process is to encapsulate the dye precursor, as a solution in a non-volatile or only slightly volatile solvent, such as chlorinated paraffin, halogenated or partially halogenated biphenyls, alkylbenzenes and/or alkylnaphthalenes, alkylated dibenzylbenzenes, high-boiling petroleum fractions, mineral oils, spindle oil or in conventional solvents such as toluene or xylene, in microcapsules and to coat the surface of the paper with these. In contact with an acid acceptor coating, a violet or blue color is produced under suitable writing or typing pressure.

The dye precursors of the present invention are markedly more soluble in the abovementioned solents than are similar compounds known in the art. Since the use of halogenated solvents, which readily dissolve the dye precursors known from the art, are objectionable in microcapsules for toxicity reasons, the good solubility of all the chromogenic compounds of the invention in other solvents, which are physiologically safer, is of great importance.

The compounds of the invention have a further advantage which is important in relation to their use as dye precursors. They show little tendency to produce a color on normal uncoated paper; hence, on making a copy, a mirror copy is not produced on the back of the top sheet coated with the dye precursor. Furthermore, the sheet coated with the microcapsules is not soiled if the capsules are unintentionally destroyed.

Because of their low tendency to sublime, the new spirodipyrans of the invention are exceptionally suitable for the manufacture of pressure-sensitive copying systems. Because of this low tendency to sublimation, the disadvantage — observable with many commercial products — that paper in direct contact with the copy also assume a coloration, is only shown to a very slight degree, if at all, by the compounds of the invention.

The examples which follow illustrate the invention; the parts are by weight.

EXAMPLE 1

254 parts of 2,3-(γ-nonyl-tetramethylene)-benzopyrylium tetrachloroferrate and 96 parts of diethylaminosalicylaldehyde in 350 parts of alcohol are refluxed for one hour. The dye solution is then introduced into a mixture of 1,000 parts of toluene and 200 parts of 25% strength ammonia solution and the batch is stirred until the color has completely disappeared. The toluene phase is separated off and concentrated to one-fifth. On adding 200 parts of isopropanol to this solution, 107 parts of colorless crystals of 3,3'-(β-nonyl-trimethylene)-7-diethyl-amino-2,2'-spirodi-[2H-1-benzopyran] are precipitated. Melting point 118°–119° C.

The same spirodipyran is obtained if in place of the pyrylium tetrachloroferrate the corresponding amount of tetrachlorozincate is used.

If a solution of this compound is dodecylbenzene is microencapsulated and coated onto a paper surface, then placed on an acid acceptor coating and written upon (whereby the capsules are destroyed and their contents brought into contact with the acceptor coating), a blue coloration results.

EXAMPLE 2

If 2,3-(γ-tert.-butyl-tetramethylene)-benzopyrylium tetrachloroferrate is condensed with an equimolar amount of diethylaminosalicylaldehyde in alcohol and the further procedure used is as in Example 1, colorless crystals of 3,3'-(β-tert.-butyl-trimethylene)-7-diethylamino-2,2'-spirodi-[2H-1-benzopyran], of melting point 120°–122° C, are obtained.

In contact with acid materials, this compound gives a blue coloration.

EXAMPLE 3

The reaction of 2,3-(γ-octyl-tetramethylene)-benzopyrylium tetrachloroferrate with diethylaminosalicylaldehyde according to Example 1 gives 3,3'-(β-octyl-trimethylene)-7-diethylamino-2,2'-spirodi-[2H-1-benzopyran] in the form of colorless crystals; melting point 136°–138° C.

In contact with acid materials, this compound gives a blue coloration.

EXAMPLE 4

55 parts of 2,3-(γ-dodecyl-tetramethylene)-benzopyrylium tetrachloroferrate and 19 parts of diethylaminosalicylaldehyde in 150 parts of alcohol are heated for 2 hours under reflux. After working up as in Example 1, colorless crystals of 3,3'-(β-dodecyl-trimethylene)-7-diethylamino-2,2'-spirodi-[2H-1-benzopyran] are obtained. Melting point 90°–92° C.

If a solution of the compound is microencapsulated and paper is coated therewith, a blue coloration is obtained if the paper is written on whilst in contact with an acid coating.

EXAMPLE 5

21 parts of 2,3-(β,δ,δ-trimethyl-tetramethylene)-benzopyrylium tetrachloroferrate and 9.6 parts of diethylaminosalicylaldehyde in 50 parts of alcohol are heated for one hour under reflux. The reaction is continued as in Example 1 and 9 parts of colorless crystals of 3,3'-(β,δ,δ-trimethyltrimethylene) 7-diethylamino-2,2'-spirodi-[2H-1-benzopyran] of melting point 138°–140° C are obtained.

In contact with acid materials, this compound gives a violet coloration.

EXAMPLE 6

If 2,3-(δ-tert.-butyl-tetramethylene)-benzopyrylium tetrachloroferrate is condensed with dimethylaminosalicylaldehyde analogously to Example 1, 3,3'-(β-tert.-butyl-trimethylene)-7-dimethylamino-2,2'-spirodi-[2H-1-benzopyran] of melting point 140°–142° C is obtained.

In contact with acid materials, this compound gives a blue coloration.

EXAMPLE 7

Reaction of 2,3-(γ-tert.-butyl-tetramethylene)-naphtho-[2,1-b]-pyrylium tetrachloroferrate with diethylaminosalicylaldehyde analogously to Example 1 gives 3,3'-(β-tert.-butyl-trimethylene)-7-diethylamino-spirodi-[2H-1-benzopyran-2,2'-[2H]-naphtho-[2,1b]-pyran].

The pale yellow crystals melt at from 180° to 180° C. In contact with acid materials, the compound develops a blue coloration.

EXAMPLES 8 TO 16

Analogously to Examples 1–7, reaction of the compounds (II) shown below with the aldehyde (IV) gives the spirodipyrans shown under (I) in column 4. These spirodipyrans give the hues mentioned in column 5 on paper provided with an acceptor coating.

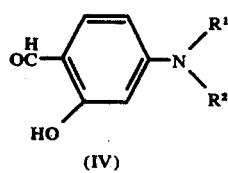

(IV)

| Example | II | | I | Hue |
|---|---|---|---|---|
| 8 | 2,3-(γ-tert.-butyl-tetramethylene)-6-chloro-benzopyrylium tetrachloroferrate | —N(C₂H₅)₂ | 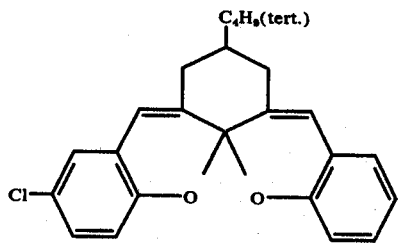 | blue |
| 9 | 2,3-(γ-dodecyl-tetramethylene)-6-bromo-benzopyrylium tetrachlorozincate | —N(C₂H₅)₂ | 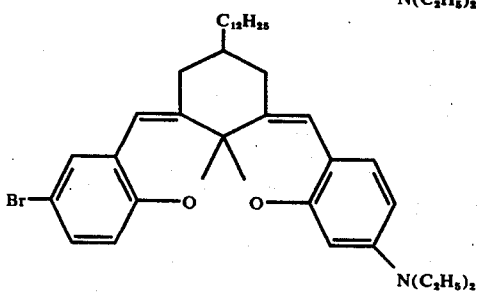 | blue |

-continued

| 10 | 2,3-(γ-tert.-butyl-tetra-methylene)-8-methoxybenzo-pyrylium tetrachloroferrate | —N(CH₃)₂ | 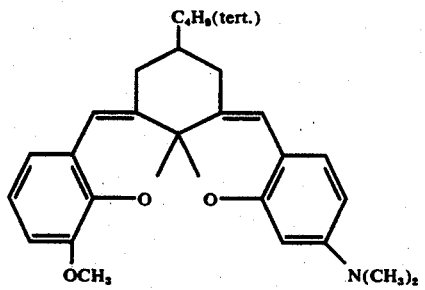 | blue-violet |
| 11 | 2,3-(γ-tert.-butyl-tetra-methylene)-6,7-dimethyl-benzopyrylium tetrachloro-ferrate | —N(CH₃)₂ | 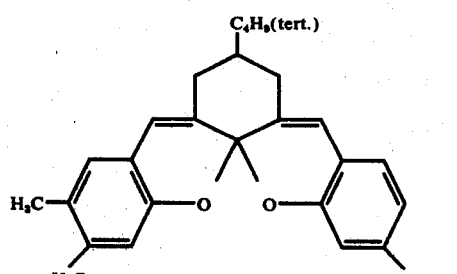 | blue |
| 12 | 2,3-(γ-octyl-tetramethyl-ene)-naphtho[2,1-b]-pyrylium-tetrachlorozincate | —N(CH₃)₂ | 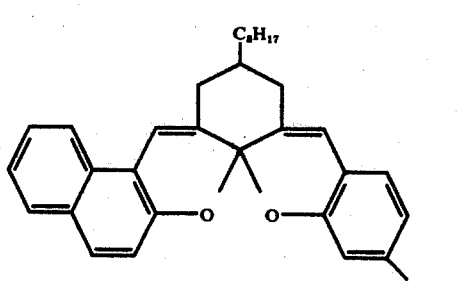 | blue |
| 13 | 2,3-(γ-tert.-butyl-tetra-methylene)-7-bromo-naphtho-[2,1-b]-pyrylium tetrachloro-ferrate | —N(C₂H₅)₂ | 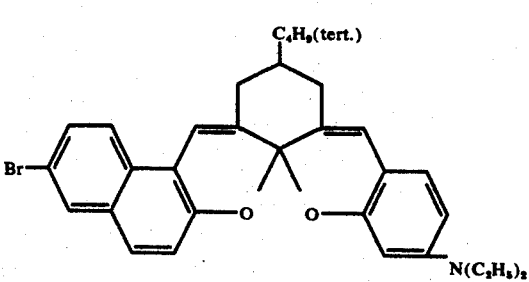 | blue |
| 14 | 2,3-(γ-tert.-butyl-tetra-methylene)-10-carbomethoxy-naphtho-[2,1-b]-pyrylium tetrachlorozincate | —N(C₂H₅)₂ | 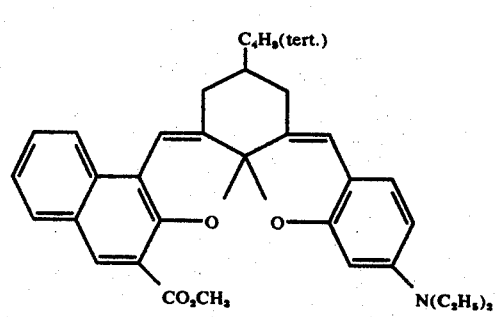 | blue |

| | | | | |
|---|---|---|---|---|
| 15 | 2,3-(β-methyl-trimethylene)-benzopyrylium tetrachloroferrate | —N(C₂H₅)₂ | 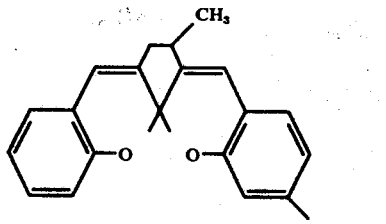 | blue-violet |
| 16 | 2,3-(γ,ε,ε-trimethyl-pentamethylene)-benzopyrylium tetrachlorozincate | —N(C₂H₅)₂ | 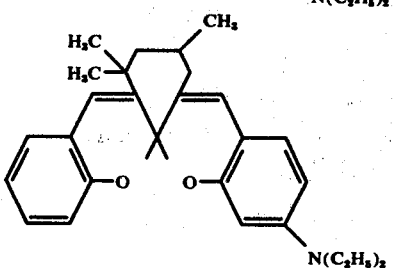 | blue |

EXAMPLE 17

48 parts of 2,3-(γ-tert.-butylcyclohexeno)-benzopyran and 39 parts of diethylaminosalicylaldehyde in 100 parts of alcohol and 20 parts of concentrated sulfuric acid are refluxed for 2 hours. The dye is precipitated at room temperature by adding 100 parts of saturated sodium acetate solution, filtered off and brought to a light color in a mixture of toluene and 25% strength ammonia solution, as described in Example 1.

35 parts of the product described in Example 2 are obtained.

2,3-(γ-tert.-butylcylcohexeno)-benzopyran was obtained as follows: 122 part of salicylaldehyde and 154 parts of tert.-butylcyclohexanone in 600 parts of concentrated sulfuric acid are heated at 50° C. The reaction mixture is then poured into 1,500 parts of ice water, whereupon the benzopyran derivative precipitates as pale yellow crystals. The precipitate is filtered off and washed neutral with water.

We claim:
1. A spirodipyran of the formula

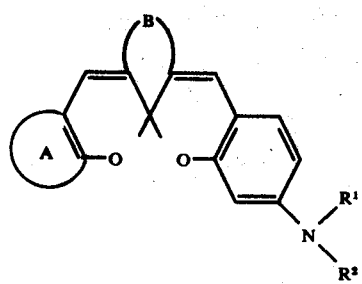

in which A is the benzene nucleus or a benzene nucleus substituted by 1 or 2 alkyl of 1 to 4 carbon atoms or one chlorine, bromine or alkoxy of 1 to 4 carbon atoms, B is dimethylene, trimethylene or tetramethylene substituted by from 1 to 3 alkyl of a total of 1 to 12 carbon atoms and R¹ and R² are identical or different alkyl, each of 1 to 6 carbon atoms.

2. A spirodipyran as claimed in claim 1, in which B is trimethylene substituted by 3 methyl or one tert.-butyl, octyl, nonyl or dodecyl and

in dimethylamino, diethylamino, dipropylamino.

3. A spirodipyran of the formula

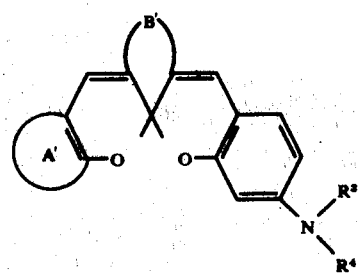

in which A' is benzene or a benzene nucleus substituted by 1 or 2 methyl or one chlorine, bromine, methoxy or ethoxy, B' is trimethylene substituted by from 1 to 3 alkyl of a total of 1 to 12 carbon atoms and R³ and R⁴ are methyl or ethyl.

4. A spirodipyran as claimed in claim 3, in which A' is the benzene nucleus and B' is trimethylene substituted by 3 methyl or one tert.-butyl, octyl, nonyl or dodecyl.

5. The spirodipyran of the formula

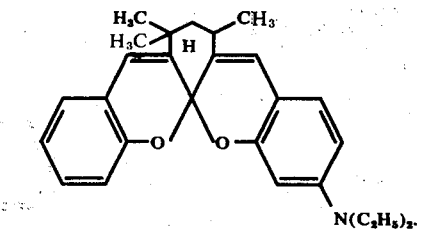

6. The spirodipyran as claimed in claim 4 of the formula

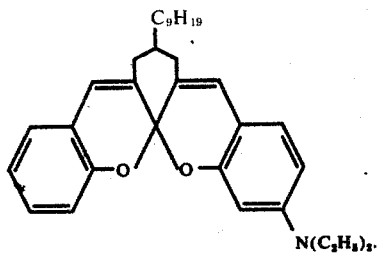
7. The spirodipyran as claimed in claim 4 of the formula
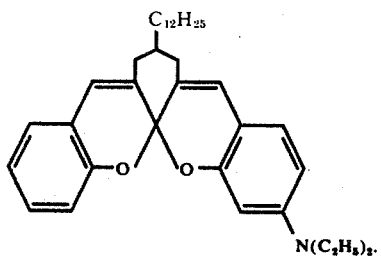
8. The spirodipyran as claimed in claim 4 of the formula
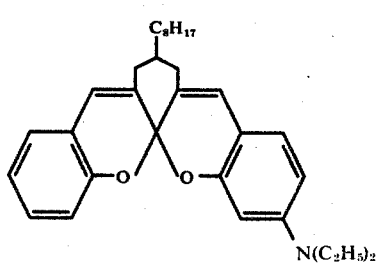
9. The spirodipyran as claimed in claim 4 of the formula
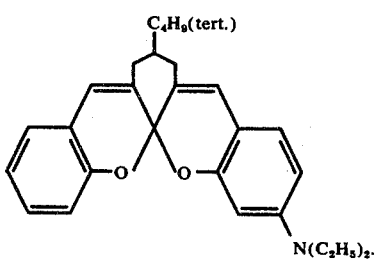
10. A spirodipyran as set forth in claim 1 wherein B is trimethylene substituted by from 1 to 3 alkyl of a total of 1 to 12 carbon atoms and $R^1$ and $R^2$ are identical or different alkyl, each of 1 to 6 carbon atoms.
* * * * *

UNITED STATES PATENT AND TRADEMARK OFFICE
CERTIFICATE OF CORRECTION

PATENT NO. : 4,029,677
DATED : June 14, 1977
INVENTOR(S) : Hans Baumann et al

It is certified that error appears in the above—identified patent and that said Letters Patent are hereby corrected as shown below:

Column 12, line 29, "in" should read --is--.

Signed and Sealed this

Eleventh Day of April 1978

[SEAL]

Attest:

RUTH C. MASON
Attesting Officer

LUTRELLE F. PARKER
Acting Commissioner of Patents and Trademarks